US00PP14482P39

(12) United States Plant Patent
Pieters

(10) Patent No.: US PP14,482 P3
(45) Date of Patent: Jan. 27, 2004

(54) CHRYSANTHEMUM PLANT NAMED 'GEDI TWO YLATL'

(50) Latin Name: *Chrysanthemum morifolium*
Varietal Denomination: Gedi Two Ylatl

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,861

(22) Filed: May 1, 2002

(65) Prior Publication Data

US 2003/0208824 P1 Nov. 6, 2003

(51) Int. Cl.[7] ..... A01H 5/00

(52) U.S. Cl. ..... Plt./295

(58) Field of Search ..... Plt./295, 286

(56) References Cited

U.S. PATENT DOCUMENTS

PP5,989 P 5/1987 Duffett et al. ..... Plt./295

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a daisy-type inflorescence, consistent flowering response to short days, blooming consistently after 49 days of short day length, free branching habit, yellow ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Ylatl.'

BACKGROUND OF THE INVENTION

The new cultivar is a natural mutation that occurred on a single branch of a plant of the Chrysanthemum cultivar 'Atlantico' (U.S. Plant patent application Ser. No. 09/550, 149, now abandoned). The new cultivar was discovered and asexually propagated by the inventor in October 1999.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Ylatl' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Ylatl'. These characteristics in combination distinguish 'Gedi Two Ylatl' as a new and distinct Chrysanthemum cultivar:

1. Daisy-type inflorescence,
2. Consistent flowering response to short days, blooming consistently after 49 days of short day length,
3. Free branching habit,
4. Yellow ray florets, 5. Very uniform round growth habit, and
6. Large quantity of blooms per flowering branch.

Plants of the new cultivar are similar to plants of the parent variety, 'Atlantico' in having pure yellow ray florets on both upper and under side. 'Atlantico' has yellow/bronze upper ray florets and the underside is bronze. The new cultivar is also slightly, but consistently, shorter.

In comparison to the commercially available variety 'Allure' (U.S. Plant Pat. No. 5,989), 'Gedi Two Ylatl' has longer lasting inflorescences, a smaller inflorescence diameter, and a free branching habit.

BRIEF DESCRIPTION OF THE PHOTOGRAPH

The photograph shows a plant of 'Gedi Two Ylatl' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the described plants was 93 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Ylatl'.

Commercial classification: Garden-type Chrysanthemum.

Parentage: Natural mutation of the Chrysanthemum cultivar 'Atlantico' (U.S. Plant patent application Ser. No. 09/550, 149, now abandoned)

PROPAGATION

Time to rooting: 7 to 14 days at approximately 21° C.
Root description: Fine, fibrous.

PLANT

Growth habit: Mounding herbaceous perennial.
Height: Approximately 18 cm.
Growth rate: Moderate.
Branching characteristics: Free Branching.
Length of lateral branches: Approximately 17 cm.
Number of leaves per lateral branch: Approximately 12.

FOLIAGE

Leaf:
- *Arrangement.*—Alternate.
- *Average length.*—Approximately 4.8 cm.
- *Average width.*—Approximately 4.3 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137C. Young foliage under side: Near 138B. Mature foliage upper side: Near 137B. Mature foliage under side: Near 138A. Venation upper side: Near 144B. Venation under side: Near 138B.
- *Venation type.*—Palmately net.

Petiole:
- *Average length.*—Approximately 2.9 cm.
- *Color.*—Near 137B.
- *Diameter.*—Approximately 0.2 cm.

BLOOM

Inflorescence:
- *Flowering habit.*—Induced by darkness period greater than 13.5 hours, approximately 49 days of appropriate day length required to induce and develop blooms.
- *Inflorescence form.*—Daisy.
- *Natural flowering season.*—Approximately the first two weeks of September.
- *Number of inflorescences per lateral branch.*—Approximately 30.
- *Inflorescence diameter.*—Approximately 3.5 cm.
- *Inflorescence depth.*—Approximately 1.1 cm.
- *Inflorescence longevity on plant.*—Approximately 28 days.
- *Persistence.*—Persistent.
- *Disc diameter.*—Approximately 1.3 cm.

Ray florets:
- *Appearance.*—Matte.
- *Texture.*—Smooth.
- *Average number per flower.*—26.
- *Shape.*—Oblong.
- *Aspect.*—Flat.
- *Margin.*—Entire.
- *Apex.*—Subacute.
- *Length.*—Approximately 1.8 cm.
- *Width.*—Approximately 0.5 cm.
- *Color.*—Upper surface at first opening: Near 5B. Upper surface at maturity: Near 5A. Upper surface at fading: Near 6A. Under surface at first opening: Near 7C. Under surface at maturity: Near 6B. Under surface at fading: Near 5C.

Disc florets:
- *Appearance.*—Shiny.
- *Texture.*—Smooth.
- *Average number per flower.*—Approximately 141.
- *Shape.*—Cylindric.
- *Apex.*—Obtuse.
- *Average length.*—Approximately 0.4 cm.
- *Average width.*—Approximately 0.1 cm.
- *Color.*—At first opening: Near 149A. At maturity: Near 12A. At fading: Near 13A.

Peduncle:
- *Length.*—At terminal end (shortest): Approximately 3.2 cm. At lateral end (longest): Approximately 13 cm.
- *Angle to stem.*—Acute.
- *Strength.*—Moderate.
- *Color.*—Near 137D.
- *Habit.*—Upright.
- *Diameter.*—Approximately 0.15 cm.
- *Surface texture.*—Lightly pubescent.

Inflorescence bud:
- *Length.*—Approximately 0.7 cm.
- *Diameter.*—Approximately 0.7 cm.
- *Form.*—Globular.
- *Color (upon emergence).*—Near 5B.

Involucral bracts (phyllaries):
- *Appearance.*—Matte.
- *Texture.*—Lightly pubescent.
- *Number.*—Approximately 22.
- *Shape.*—Ovate.
- *Margin.*—Entire.
- *Apex.*—Subacute.
- *Length.*—Approximately 0.7 cm.
- *Width.*—Approximately 0.4 cm.
- *Color.*—Upper side: Near 143A. Under side: Near 143A.

REPRODUCTIVE ORGANS

Ray florets:
- *Number of pistils per flower.*—1.
- *Stigma shape.*—2 branched.
- *Stigma color.*—Near 12A.
- *Style color.*—Near 3C.
- *Style length.*—Approximately 0.4 cm.
- *Stamens.*—Absent.

Disc florets:
- *Number of pistils per flower.*—1.
- *Stigma shape.*—Two-branched.
- *Stigma color.*—Near 13B.
- *Style length.*—Approximately 0.3 cm.
- *Style color.*—Near 7D.
- *Number of stamens per flower.*—5.
- *Anther shape.*—Tubular.
- *Anther color.*—Near 13B.
- *Pollen color.*—Near 13B.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Ylatl' as herein illustrated and described.

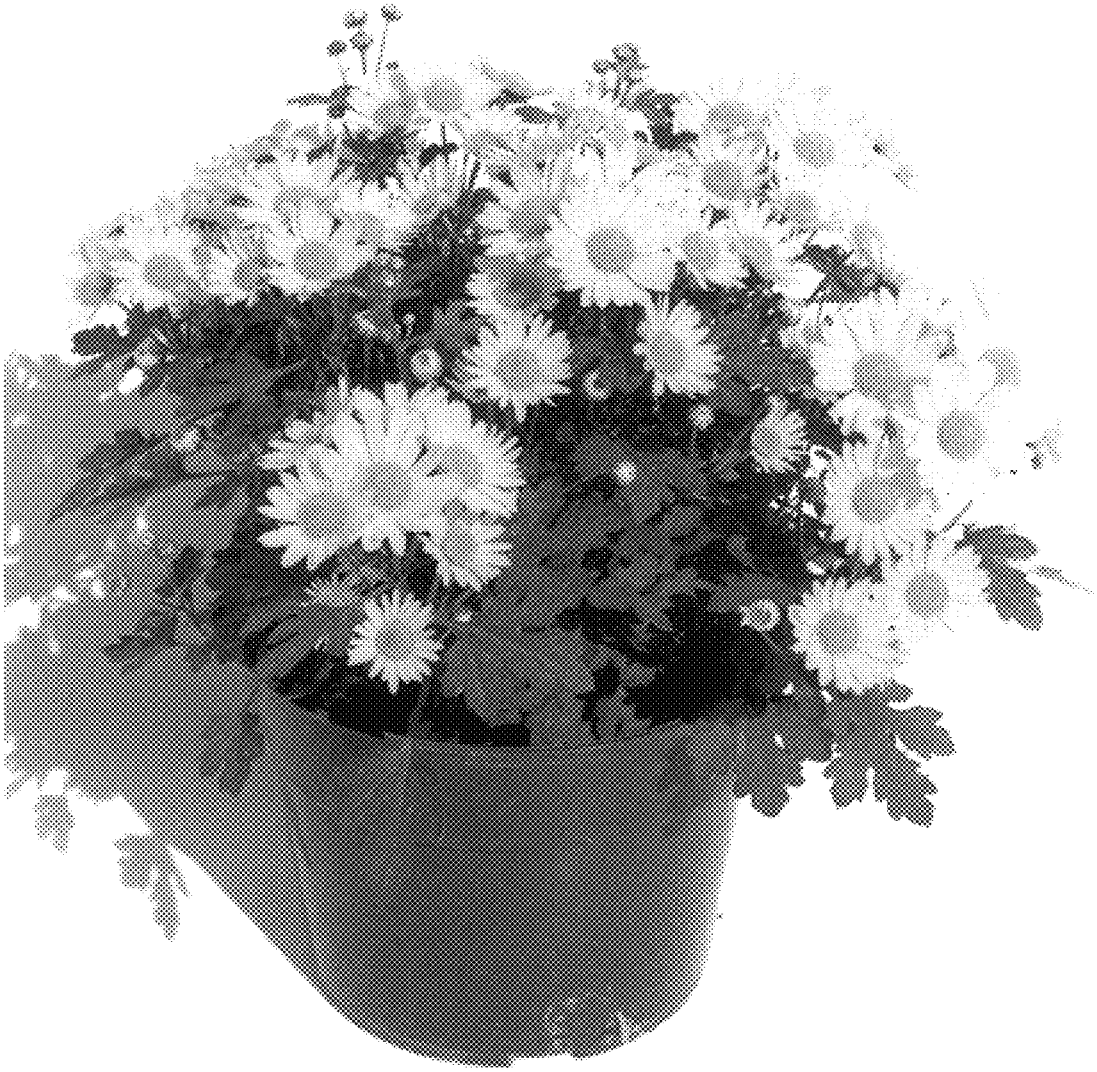

* * * * *